United States Patent
Iaccino et al.

(10) Patent No.: US 11,701,645 B2
(45) Date of Patent: Jul. 18, 2023

(54) CALCINATION OF MICROPOROUS MOLECULAR SIEVE CATALYSTS

(71) Applicant: ExxonMobil Chemical Patents Inc., Baytown, TX (US)

(72) Inventors: Larry L. Iaccino, Seabrook, TX (US); Jeremy W. Bedard, Humble, TX (US); Xiaoying Bao, Houston, TX (US); Andrew P. Palermo, Houston, TX (US); Nitish Mittal, Houston, TX (US); Maria Milina, Houston, TX (US); Doron Levin, Highland Park, NJ (US); William R. Gunther, Clinton, NJ (US); Wenyih F. Lai, Bridgewater, NJ (US); Tilman W. Beutel, Neshanic Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 266 days.

(21) Appl. No.: 17/284,636

(22) PCT Filed: Oct. 10, 2019

(86) PCT No.: PCT/US2019/055538
§ 371 (c)(1),
(2) Date: Apr. 12, 2021

(87) PCT Pub. No.: WO2020/091968
PCT Pub. Date: May 7, 2020

(65) Prior Publication Data
US 2021/0394163 A1 Dec. 23, 2021

Related U.S. Application Data

(60) Provisional application No. 62/752,549, filed on Oct. 30, 2018.

(51) Int. Cl.
*B01J 29/44* (2006.01)
*B01J 6/00* (2006.01)
(Continued)

(52) U.S. Cl.
CPC ............... *B01J 29/44* (2013.01); *B01J 6/002* (2013.01); *B01J 8/0285* (2013.01); *B01J 29/46* (2013.01);
(Continued)

(58) Field of Classification Search
CPC . B01J 29/44; B01J 6/002; B01J 8/0285; B01J 29/46; B01J 37/0009; B01J 37/0207;
(Continued)

(56) References Cited

U.S. PATENT DOCUMENTS 7,238,636 B2  7/2007  Beck et al. ................... 502/63
8,956,588 B2  2/2015  Armitage et al. ............ 423/700
(Continued)

FOREIGN PATENT DOCUMENTS

EP          0186479       8/1989    ............ B01J 29/32

OTHER PUBLICATIONS

Emeis, C. A. (1993) "Determination of Integrated Molar Extinction Coefficients for Infrared Absorption Bands of Pyridine Adsorbed on Solid Acid Catalysts," *J. Catal.*v.141(2), pp. 347-354.

*Primary Examiner* — Ali Z Fadhel

(57) ABSTRACT

A catalyst comprising a microporous crystalline metallosilicate having a Constraint Index of 12, or 10, or 8, or 6 or less, a binder, a Group 1 alkali metal or a compound thereof and/or a Group 2 alkaline earth metal or a compound thereof, a Group 10 metal or a compound thereof, and, optionally, a Group 11 metal or a compound thereof; wherein the catalyst is calcined in a first calcining step before the addition of the Group 10 metal or compound thereof and optionally the Group 11 metal or compound (Continued)

thereof; and wherein the first calcining step includes heating the catalyst to first temperatures of greater than 500° C.; and wherein the catalyst is calcined in a second calcining step after the addition of the Group 10 metal or compound thereof and optionally the Group 11 metal or compound thereof wherein the second calcining step includes heating the catalyst to temperatures of greater than 400° C.

20 Claims, 1 Drawing Sheet

(51) Int. Cl.
*B01J 8/02* (2006.01)
*B01J 29/46* (2006.01)
*B01J 37/00* (2006.01)
*B01J 37/02* (2006.01)
*B01J 37/04* (2006.01)
*B01J 37/08* (2006.01)
*C07C 5/373* (2006.01)

(52) U.S. Cl.
CPC ....... *B01J 37/0009* (2013.01); *B01J 37/0207* (2013.01); *B01J 37/04* (2013.01); *B01J 37/082* (2013.01); *C07C 5/373* (2013.01); *C07C 2529/44* (2013.01); *C07C 2529/46* (2013.01)

(58) Field of Classification Search
CPC ............ B01J 37/04; B01J 37/082; B01J 2208/00123; B01J 8/1836; B01J 2208/065; B01J 6/004; B01J 23/50; B01J 23/72; B01J 23/8926; B01J 23/42; B01J 37/08; B01J 8/067; B01J 8/26; B01J 29/48; B01J 29/90; B01J 37/0018; B01J 37/0201; C07C 5/373; C07C 2529/44; C07C 2529/46; C07C 2/44; C07C 5/03; C07C 13/15

See application file for complete search history.

(56) References Cited

U.S. PATENT DOCUMENTS

| | | | |
|---|---|---|---|
| 9,849,440 B2 | 12/2017 | Iaccino et al. | B01J 21/08 |
| 9,856,187 B2 | 1/2018 | Iaccino et al. | C07C 5/373 |
| 9,873,647 B2 | 1/2018 | Iaccino | C07C 5/373 |
| 9,896,395 B2 | 2/2018 | Iaccino et al. | C07C 5/373 |
| 9,896,396 B2 | 2/2018 | Iaccino et al. | C07C 5/373 |
| 9,908,825 B1 | 3/2018 | Iaccino et al. | C07C 5/373 |
| 9,914,678 B2 | 3/2018 | Iaccino et al. | C07C 5/373 |
| 9,919,988 B2 | 3/2018 | Iaccino et al. | C07C 5/373 |
| 9,926,242 B2 | 3/2018 | Iaccino et al. | C07C 5/373 |
| 9,988,324 B2 | 6/2018 | Iaccino et al. | C07C 5/373 |
| 9,994,499 B2 | 6/2018 | Iaccino et al. | C07C 5/373 |
| 10,011,539 B2 | 7/2018 | Iaccino et al. | C07C 5/373 |
| 10,155,702 B2 | 12/2018 | Iaccino et al. | C07C 5/373 |
| 10,155,703 B2 | 12/2018 | Iaccino et al. | C07C 5/373 |
| 10,202,318 B2 | 2/2019 | Shekhar et al. | C07C 2/76 |
| 10,280,127 B1 | 5/2019 | Iaccino et al. | C07C 5/373 |
| 10,294,175 B2 | 5/2019 | Iaccino et al. | C07C 5/373 |
| 10,364,200 B2 | 7/2019 | Sangar et al. | C07C 5/3337 |
| 10,611,705 B2 | 4/2020 | Iaccino et al. | C07C 5/3337 |
| 10,821,427 B2 | 11/2020 | Bedard et al. | B01J 29/90 |
| 2013/0008827 A1* | 1/2013 | Nagayasu | B01J 37/0201 502/66 |
| 2013/0225876 A1* | 8/2013 | Weiner | C07C 29/149 502/328 |
| 2015/0025283 A1 | 1/2015 | Cheng et al. | C07C 6/06 |
| 2018/0318813 A1 | 11/2018 | Iaccino et al. | B01J 29/90 |
| 2018/0319717 A1 | 11/2018 | Sangar et al. | C07C 2/52 |
| 2020/0239384 A1 | 7/2020 | Sangar et al. | C07C 2/84 |
| 2021/0002186 A1 | 1/2021 | Iaccino et al. | C07C 5/321 |

* cited by examiner

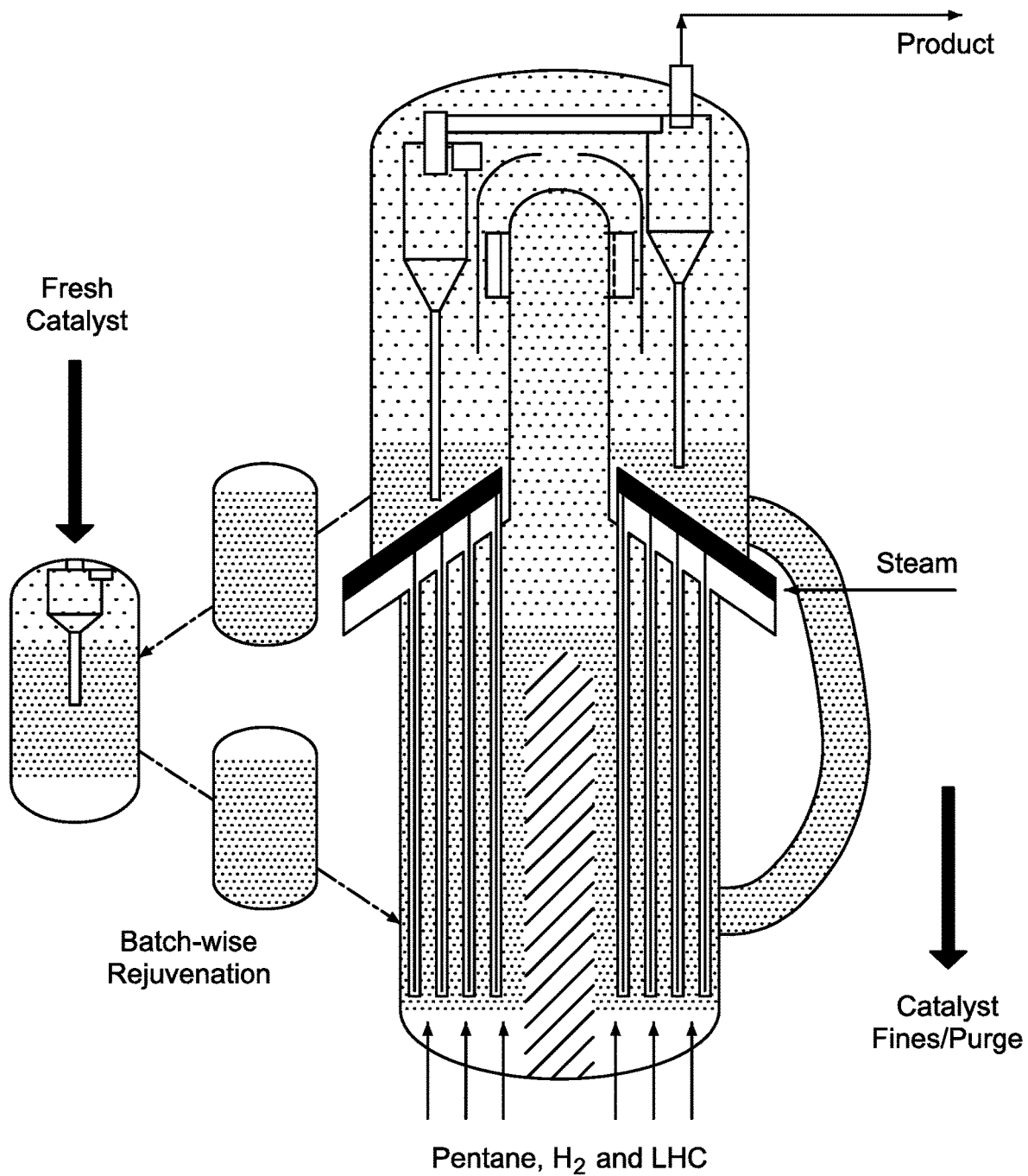

US 11,701,645 B2

CALCINATION OF MICROPOROUS MOLECULAR SIEVE CATALYSTS

PRIORITY

This application is a national stage filing of Patent Cooperation Treaty Application No. PCT/US2019/055538, filed Oct. 10, 2019, which claims priority to U.S. Provisional Application No. 62/752,549, filed Oct. 30, 2018, the disclosure of which is incorporated herein by reference.

FIELD

The present invention relates in general to microporous molecular sieves and methods of making them, and more particularly to zeolites and zeolite catalyst formulations useful to convert acyclic alkanes to cyclic alkanes.

BACKGROUND

Microporous molecular sieves are crystalline silicates having a three-dimensional interconnecting network of silica tetrahedra. A portion of the silica atoms may be replaced with other elements such as aluminum, boron, gallium, indium, germanium, tin, iron, copper, silver, and/or zinc to form a microporous crystalline metallosilicate. Natural water of hydration is removed from this network by heating to produce uniform cavities which selectively adsorb molecules of a specific size. One particular use for microporous crystalline metallosilicates is in the cyclization of acyclic alkanes, especially C4 to C10 alkanes, most preferably five-carbon (C5s) hydrocarbons. For commercial use, microporous crystalline metallosilicates crystals must be formulated into catalysts usable in commercial reactors. To form a catalyst, the microporous crystalline metallosilicates are typically combined with inert binders and made into some usable form. Desirable physical forms include extrudates, wash-coated tubes and monoliths, and fluidizable particles.

Catalyst formulations should have positive or at least minimally negative effects on catalyst activity, selectivity, and aging. Thus, it would be desirable to have a formulated microporous crystalline metallosilicates catalyst that could achieve these ends.

The present application is related to U.S. Ser. No. 62/500,814 filed May 3, 2017, incorporated herein by reference.

BRIEF DESCRIPTION OF THE DRAWING

The FIGURE is a schematic diagram of a fluid bed reactor and exemplary process and conditions for converting compounds such as pentane into cyclic olefins, as well as the rejuvenation of the catalyst used in the process.

SUMMARY

Described is a catalyst comprising (or consisting of, or consisting essentially of) a microporous crystalline metallosilicate having a Constraint Index of 12, or 10, or 8, or 6 or less, a binder, a Group 1 alkali metal or a compound thereof and/or a Group 2 alkaline earth metal or a compound thereof, a Group 10 metal or a compound thereof, and, optionally, a Group 11 metal or a compound thereof; wherein the catalyst is calcined in a first calcining step before the addition of the Group 10 metal or compound thereof and optionally the Group 11 metal or compound thereof; and wherein the catalyst is calcined in a second calcining step after the addition of the Group 10 metal or compound thereof and optionally the Group 11 metal or compound thereof; and wherein the first calcining step includes heating the catalyst to temperatures of greater than 500° C. and the second calcining step includes heating the catalyst to temperatures greater than 400° C.

DETAILED DESCRIPTION

It has been discovered that high severity calcination, or simply "calcining" as described herein, is required in two distinct steps to maximize activity of formulated catalyst. The severity is defined by a combination of calcination temperature and calcination time as it is hypothesized to be a kinetic effect. A first high severity calcination step is required after formulation of the catalyst wherein the microporous crystalline metallosilicate is combined with a binder. This first calcination step serves multiple purposes including, but not limited to, removal of the organic structure directing agent from the microporous crystalline metallosilicate, hardening the binder, and generating silanol defects in the microporous crystalline metallosilicate. After the addition of the Group 10 metal or compound thereof, and optionally the Group 11 metal or compound thereof, a second high severity calcination step is required. This second calcination step serves multiple purposes including, but not limited to, decomposition of the metal salt and migration of the metal or metals to preferred anchoring sites. There is also a maximum severity that is desirable as it is hypothesized that there are at least two competing effects: (1) where at least a portion of the Group 10 metal is first on the binder portion of the formulated catalyst, that metal may migrate from the binder to inside the microporous crystalline metallosilicates crystals where it is more active for cyclization; and (2) where the Group 10 metal anchors on silanol defects and/or other anchoring sites within the microporous crystalline metallosilicates crystal itself, these silanol sites may anneal with higher severity.

Thus, in any embodiment the invention described herein is a catalyst comprising (or consisting of, or consisting essentially of): (i) a microporous crystalline metallosilicate having a Constraint Index of 12, or 10, or 8, or 6 or less, (ii) a binder, (iii) a Group 1 alkali metal or a compound thereof and/or a Group 2 alkaline earth metal or a compound thereof, (iv) a Group 10 metal or a compound thereof, and, (v) optionally, a Group 11 metal or a compound thereof; wherein the catalyst is calcined in a first calcining step before the addition of the Group 10 metal or compound thereof and optional Group 11 metals or compound thereof; and wherein the catalyst is calcined in a second calcining step after the addition of the Group 10 metal or compound thereof and optionally the Group 11 metal or compound thereof; and wherein the first calcining step includes heating the catalyst to temperatures of greater than 500° C. and the second calcining step includes heating the catalyst to temperatures greater than 400° C. when to the optional Group 11 metal is not present, and includes heating the catalyst to temperatures of greater than 500° C. when the optional Group 11 metal is present.

As used herein "Group" refers to Groups of the Periodic Table of Elements as in HAWLEY'S CONDENSED CHEMICAL DICTIONARY, Thirteenth Edition (1997 John Wiley & Sons, Inc.).

As used herein, the "Constraint Index" is a measure of the extent to which a microporous molecular sieve (e.g., zeolites, aluminosilicates) provides controlled access of different sized molecules to its internal structure. For example, molecular sieves which provide a highly restricted access to and egress from its internal structure have a high value for the Constraint Index, and molecular sieves of this kind usually have pores of small size, e.g. less than 5 Angstroms. On the other hand, molecular sieves which provide relatively free access to the internal molecular sieves structure have a low value for the Constraint Index, and usually pores of large size.

A determination of the Constraint Index is made by continuously passing a mixture of an equal weight of n-hexane and 3-methylpentane over a small molecular sieves catalyst sample, approximately 1 gram or less, of catalyst at atmospheric pressure. A sample of the catalyst, in the form of pellets or extrudate, is crushed to a particle size about that of coarse sand and mounted in a glass tube. Prior to testing, the catalyst is treated with a stream of air at 1000° F. (538° C.) for at least 15 minutes. The catalyst is then flushed with helium and the temperature adjusted between 550° F. (288° C.) and 950° F. (510° C.) to give an overall conversion between 10% and 60%. The mixture of hydrocarbons is passed at 1 liquid hourly spaced velocity (i.e., one volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons. The Constraint Index is then calculated using the following equation: Constraint Index=$Log_{10}$ (fraction of n-hexane remaining)/$Log_{10}$ (fraction of 3-methylpentane remaining).

The Constraint Index approximates the ratio of the cracking rate constants for the two hydrocarbons. Catalysts suitable for the present invention are those having a constraint index in the approximate range of 1 to 12. Constraint Index (CI) values for some typical catalysts are: Erinotite (38); ZSM-5 (8.3); ZSM-11 (8.7); ZSM-12 (2); ZSM-38 (2); ZSM-38 (4.5); synthetic Mordenite (0.5); REY (0.4); amorphous aluminosilicate (0.6).

As used herein, the "Alpha Value" of a molecular sieve catalyst is a measure of the cracking activity of that catalyst. Catalytic cracking activity is typically indicated by the weight to percent conversion of hexane to lower boiling C1 to C5 hydrocarbons, while isomerization activity is indicated by weight percent conversion to hexane isomerization. The Alpha Value is an approximate indication of the catalytic cracking activity of the catalyst compared to a standard amorphous aluminosilicate catalyst obtained by co-gellation, 10% alumina, surface area of 420 $m^2$/g, no cations in base exchanging solution. The cracking activity is obtained as a relative rate constant, the rate of n-hexane conversion per unit volume of oxides composition per unit time. This highly active aluminosilicate catalyst has an Alpha Value taken as 1. The experimental conditions of the test include heating the catalyst to a constant temperature of 538° C., and passing the hexane over the solid catalyst at that temperature at a variable flow rate to give contact times between 10 and $10^{-3}$ seconds. The tested particles should be smaller than 30 mesh in size, preferably 12 to 28 mesh. Alpha Values for some typical catalysts are: ZSM-5 with no cation exchange (38), and with $H^+$ exchange (450); synthetic Faujasite exchanged in calcium ions (1.1), and exchanged in $H(NH_4)$ (6,400).

When referring to "calcining" herein, this feature, action or process can take place within a period of time, that is, the catalyst or components being "calcined" are exposed to the specified temperature or at a temperature within the specified range, constant or varying within the range, for a period of time. That time may vary within a range from 20 minutes, or 30 minutes, or 1 hour, or 2 hours, to 6 hours, or 8 hours, or 10 hours. The calcination may be performed in a rotary calciner or a fixed bed calciner in an air atmosphere (oxygen/nitrogen, either directly from the atmosphere or otherwise provided) or with an atmosphere with the oxygen content adjusted.

In any embodiment, as described above, the first calcining step is carried out at a temperature greater than 500, or 525, or 550° C., or within a range from 500, or 525, or 550, or 575° C. to 600, or 650, or 700, or 800° C.; and wherein the second calcining step is carried out at a temperature greater than 400, or 425, or 450, or 475° C., or within a range from 400, or 425, or 450, or 475, or 500, or 550° C. to 650, or 700, or 750, or 800, or 850, or 900, or 1000° C.

To be used as a commercially viable catalyst, the microporous metallosilicate is combined with some binder, preferably a material that resists chemical reactions and physical changes due to heat, and further, can provide rigid structure for the microporous metallosilicate. Thus, in any embodiment, the binder is selected from silica, titania, zirconia, alkali metal silicates, Group 13 metal silicates, carbides, nitrides, aluminum phosphate, aluminum molybdate, aluminate, surface passivated alumina, and mixtures thereof. In any embodiment, the catalyst is formed into one or more of the shapes of extrudates (cylindrical, lobed, asymmetric lobed, spiral lobed), spray dried particles, oil drop particles, mulled particles, spherical particles, and/or wash coated substrates; wherein the substrates may be extrudates, spherical particles, foams, microliths and/or monoliths.

Catalyst compositions useful herein include microporous crystalline metallosilicates, such as crystalline aluminosilicates, crystalline ferrosilicates, or other metal containing crystalline silicates (such as those where the metal or metal containing compound is dispersed within the crystalline silicate structure and may or may not be a part of the crystalline framework. Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from groups 8, 11 and 13 of the Periodic Table of the Elements (preferably one or more of Fe, Cu, Ag, Au, B, Al, Ga, and or In) are incorporated in the crystal structure during synthesis or impregnated post crystallization. It is recognized that a metallosilicate may have one or more metals present and, for example, a material may be referred to as a ferrosilicate but it will most likely still contain small amounts of aluminum.

The microporous crystalline metallosilicates preferably have a constraint index in the range of 3 to 12.

Aluminosilicates useful herein having a constraint index of 3 to 12 include and are selected from the group consisting of ZSM-5, ZSM-11, ZSM-22, ZSM-23, ZSM-35, ZSM-48, ZSM-50, ZSM-57, ZSM-58, a MCM-22 family material and mixtures of two or more thereof. Preferably, the microporous crystalline aluminosilicate that has a constraint index in the range of 3 to 12 is ZSM-5. ZSM-5 is described in U.S. Pat. No. 3,702,886. ZSM-11 is described in U.S. Pat. No. 3,709,979. ZSM-22 is described in U.S. Pat. No. 5,336,478.

ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829, and ZSM-57 is described in U.S. Pat. No. 4,873,067. ZSM-58 is described in U.S. Pat. No. 4,698,217.

The MCM-22 family aluminosilicates are selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures of two or more thereof.

Aluminosilicates of the MCM-22 family include MCM-22 described in U.S. Pat. No. 4,954,325, PSH-3 described in U.S. Pat. No. 4,439,409, SSZ-25 described in U.S. Pat. No. 4,826,667, ERB-1 described in EP 0293032, ITQ-1 described in U.S. Pat. No. 6,077,498, and ITQ-2 described in WO 97/17290, MCM-36 described in U.S. Pat. No. 5,250,277, MCM-49 described in U.S. Pat. No. 5,236,575, MCM-56 described in U.S. Pat. No. 5,362,697 and mixtures of two or more thereof. Related zeolites to be included in the MCM-22 family are UZM-8 described in U.S. Pat. No. 6,756,030 and UZM-8HS described in U.S. Pat. No. 7,713,513, both of which are also suitable for use as the molecular sieve of the MCM-22 family.

In one or more embodiments, the crystalline metallosilicate has an Si/M molar ratio (where M is a Group 8, 11 or 13 metal) greater than 25, or greater than 50, or greater than 100, or greater than 400, or greater than 1,000, or in the range from 100 to 2,000, or from 100 to 1,500, or from 50 to 2,000, or from 50 to 1,200.

In one or more embodiments, the porous crystalline metallosilicate is crystalline aluminosilicate having a $SiO_2/Al_2O_3$ molar ratio greater than 25, or greater than 50, or greater than 100, or greater than 400, or greater than 1,000, or in the range from 25 to 2,000, or from 50 to 1,500, or from 100 to 1,000, or from 100 to 800, or from 200 to 600, or from 300 to 600.

The Group 10 metal is selected from the group consisting of nickel, palladium and platinum, preferably platinum. The Group 10 metal content of said catalyst composition is at least 0.005 wt %, based on the weight of the catalyst composition. The Group 10 content is in the range from 0.005 wt % to 10 wt %, or from 0.005 wt % up to 1.5 wt %, based on the weight of the catalyst composition.

Optionally, the Group 10 metal is present in combination with an additional metal selected from Groups 8, 9, and 11 of the Periodic Table of the Elements and the rare earth metals, such as Ga, In, Zn, Cu, Re, Mo, W, La, Fe, Ag, Pd, Rh, Pr, La, and/or oxides, sulfides, nitrides, and/or carbides of these metals. Alternatively or additionally, the Group 10 metal is present in combination with a Group I alkali metal and/or a Group 2 alkaline earth metal.

A preferred Group 9 metal is Rh, which may form an alloy with the Group 10 metal. Preferably, the molar ratio of Rh to Group 10 metal is in the range from 0.1 to 5.

Typically, the rare earth metal is selected from the group consisting of yttrium, lanthanum, cerium, praseodymium, and mixtures or combinations thereof. Preferably, the molar ratio of rare earth metal to Group 10 metal is in the range from 1 to 10. The rare earth metal may be added to the catalyst composition during or after synthesis of the microporous crystalline molecular sieve as any suitable rare earth metal compound.

Preferred additional metals are Group 11 metals. Typically, the Group 11 metal is selected from the group consisting of Cu, Ag, Au, and mixtures of two or more thereof; preferably Cu or Ag. The Group 11 metal content of the catalyst composition is such that the molar ratio of Group 11 metal to Group 10 metal is at least 0.01, based on the molar quantities of each in the catalyst composition. Preferably, the molar ratio of Group 11 metal to Group 10 metal is in the range from 0.1 to 10 or from 0.5 to 5 based on the molar quantities of each in the catalyst composition. The Group 11 metal may be added to the catalyst composition during or after synthesis of the microporous crystalline molecular sieve as any suitable Group 11 metal compound.

In one or more embodiments, the catalyst composition has an Alpha Value (as measured prior to the addition of the Group 10 metal, preferably platinum) of less than 25, preferably of less than 15.

Generally, the Group 1 alkali metal and/or the Group 2 alkaline earth metal is present as an oxide. The Group 1 alkali metal includes, or is selected from the group consisting of lithium, sodium, potassium, rubidium, caesium, and mixtures of two or more thereof, preferably sodium. The Group 2 alkaline earth metal, includes, or is selected from the group consisting of beryllium, magnesium, calcium, strontium, barium, and mixtures of two or more thereof.

In one or more embodiments, the molar ratio of said Group 1 alkali metal to aluminum is at least 0.5, or at least 1, or in the from at least 1 up to 3, preferably at least 2, more preferably at least 3. In one or more embodiments, the molar ratio of said Group 2 alkaline earth metal to aluminum is at least 0.5, or at least 1, or from at least 1 up to 3, preferably at least 2, more preferably at least 3.

Useful catalyst compositions comprise a crystalline aluminosilicate, which is optionally combined with one, two, or more additional metals or metal compounds. Preferred combinations include: platinum on MFI silversilicate, platinum on coppersilicate MFI, platinum with silver on ZSM-5, and platinum with copper on ZSM-5.

In any embodiment the microporous crystalline metallosilicate comprises a metallosilicate framework type selected from the group consisting of MWW, MFI, LTL, MOR, BEA, TON, MTW, MTT, FER, MRE, MFS, MEL, DDR, EUO, and FAU.

In any embodiment, the microporous crystalline metallosilicate is an aluminosilicate selected from the group consisting of Zeolite beta, mordenite, faujasite, Zeolite L, ZSM-5, ZSM-11, ZSM-30, ZSM-22, ZSM-23, ZSM-35, ZSM-48, ZSM-50, ZSM-57, ZSM-58, MCM-22 family material, and mixtures thereof.

In any embodiment, the molar ratio of the Group 1 alkali metal to aluminum is at least 1, and/or the molar ratio of the Group 2 alkaline earth metal to aluminum is at least 1 and the Group 1 alkali metal is selected from the group consisting of lithium, sodium, potassium, rubidium, cesium, and mixtures of two or more thereof, and/or the Group 2 alkaline earth metal is selected from the group consisting of beryllium, magnesium, calcium, strontium, barium, and mixtures thereof.

In any embodiment, the catalyst has an Alpha Value (as measured prior to the addition of the Group 10 metal, and/or prior to the addition of the optional Group 11 metal) of less than 14, or 16, or 18, or 20, or 25. In any embodiment, the Group 10 metal is platinum, and wherein the platinum is derived from compounds selected from the group consisting of platinum nitrate, chloroplatinic acid, platinous chloride, platinum amine compounds, tetraamine platinum hydroxide, and mixtures thereof.

In any embodiment, the optional Group 11 metal is copper, and wherein the copper is derived from compounds selected from the group consisting of copper nitrate, copper nitrite, copper acetate, copper hydroxide, copper acetylacetonate, copper carbonate, copper lactate, copper sulfate, copper phosphate, copper chloride, and mixtures thereof; and/or the Group 11 metal is silver, wherein the silver derived from a compound selected from the group consisting of silver nitrate, silver nitrite, silver acetate, silver hydroxide, silver acetylacetonate, silver carbonate, silver lactate, silver sulfate, silver phosphate, and mixtures thereof.

Over the course of the hydrocarbon conversion processes described herein, the activity of the catalyst generally gradually declines to form a deactivated catalyst due to the accumulation of carbonaceous or coke material and/or agglomeration of metal on the catalyst material during the reaction. It has presently been discovered that deactivation due to metal agglomeration occurs at a slower rate than deactivation due to coke formation during the course of the hydrocarbon conversion processes. Thus, in any embodiment, as with most microporous metallosilicates, the catalyst is periodically rejuvenated and/or regenerated. This may be done in a vessel separate from the catalytic function of the catalyst, or in the same vessel as the primary catalytic function of the catalyst, such as the conversion of acyclic C5s to cyclic C5 compounds.

As such, a rejuvenation cycle is advantageously performed to produce a rejuvenated catalyst having restored or substantially restored catalyst activity, typically by removing at least a portion of the incrementally deposited coke material from the catalyst composition. Preferably, rejuvenated catalyst has activity restored to at least 50% of the activity of the catalyst prior to deactivation, more preferably at least 60%, more preferably at least 80%. Rejuvenated catalyst also preferably has restored or substantially restored catalyst selectivity, e.g., selectivity restored to at least 50% of the selectivity of the catalyst prior to deactivation, more preferably at least 60%, more preferably at least 80%. As used herein, "incrementally deposited coke" refers to the amount of coke that is deposited on the catalyst during a conversion cycle. Typically, a rejuvenation cycle is employed when the catalyst composition comprises >1 wt % incrementally deposited coke, such as >5 wt % incrementally deposited coke, or >10 wt % incrementally deposited coke. This is described in more detail in U.S. Ser. No. 62/500,795 filed May 2, 2017, incorporated herein by reference.

In any embodiment, the calcination described herein is performed at least partially in conjunction with the process unit where the converting of acyclic C5s to cyclic C5 compounds is performed. Further, in any embodiment the second high temperature calcination may be done in the rejuvenation vessel on the far left of the FIGURE. Preferably the catalyst inventory will be circulating from the reactor through the batch wise rejuvenation vessels such as shown in FIGURE. Potentially fresh catalyst could be added to the circulating catalyst and the second high temperature calcination performed with the fresh catalyst comingled with the circulating catalyst. Alternatively, occasionally circulating catalyst could be halted and a batch of fresh catalyst could be subjected to the second calcination step neat.

In any embodiment, the catalyst described herein is combined with acyclic C5s to form cyclic C5 compounds including cyclopentadiene. In any embodiment, the acyclic C5 conversion conditions include at least a temperature of 450° C. to 650° C., the molar ratio of the optional $H_2$ co-feed to the acyclic C5 feedstock is in the range of 0.01 to 3, the molar ratio of the optional light hydrocarbon co-feed to the acyclic C5 feedstock is in the range of 0.01 to 5, the acyclic C5 feedstock has a partial pressure in the range of 3 psia to 100 psia (21 to 689 kPa-a) at the reactor inlet, and the acyclic C5 feedstock has a weight hourly space velocity in the range from 1 $hr^{-1}$ to 50 $hr^{-1}$.

In any embodiment, suitable hydrocarbon conversion processes can be conducted in a wide range of reactor configurations. Particularly preferred reactor configurations include convectively heated tubes (as described in U.S. Pat. No. 9,926,242); fired tubes (as described in U.S. Pat. No. 9,914,678); a riser reactor (as described in US 2017/0121252); a circulating fluidized bed or a circulating settling bed with counter-current flow (as described in U.S. Pat. No. 9,908,825); a cyclic fluidized bed reactor or a cyclic fixed bed reactor (as described in US 2017/0121251); and/or an electrically heated reactor. In addition, suitable hydrocarbon conversion processes can be conducted in a single reaction zone or in a plurality of reaction zones, such as an adiabatic reaction zone followed by a diabatic reaction zone (as described in U.S. Pat. No. 9,873,647).

In any embodiment, the acyclic C5 conversion occurs in one of more reactors selected from radiantly heated tubular reactor, convectively heated tubular reactor, cyclically reheated fixed bed reactor, circulating fluid bed reactor, radiantly heated fluid bed reactor, convectively heated fluid bed reactor, adiabatic reactor and/or electrically heated reactor. An example of a suitable reactor is shown in the FIGURE.

An article can be formed from cyclic C5 compounds described herein. In any embodiment the article is derived from a Diels-Alder reaction of the cyclic C5 compounds with a double bond containing compound. In any embodiment, the cyclic C5 compounds are selected from the group consisting of cyclopentadiene, dicyclopentadiene, cyclopentene, cyclopentane, substituted norbornenes, Diels Alder reaction derivatives of cyclopentadiene, cyclic olefin copolymers, cyclic olefin polymers, polycyclopentene, unsaturated polyester resins, hydrocarbon resin tackifiers, formulated epoxy resins, polydicyclopentadiene, metathesis polymers of norbornene or substituted norbornenes or dicyclopentadiene, and combinations thereof. In any embodiment, the article is selected from the group consisting of wind turbine blades, composites containing glass or carbon fibers, formulated adhesives, ethylidene norbornene, ethylene-propylene rubber, ethylene-propylene-diene rubber alcohols, plasticizers, blowing agents, solvents, octane enhancers, gasoline, and mixtures thereof.

EXAMPLES

Part 1 Examples: Impact of Second Step Calcining

Example 1.0: Comparative example calcined 3 hours in air at 350° C., Ag/Pt. A mixture with about 22% solids was prepared from 8,800 g of deionized water, 600 g of 50% NaOH solution, 26 g of 43% Sodium Aluminate solution, 730 g of n-propyl amine (n-PA) 100% solution, 20 g of ZSM-5 seed crystals, and 3,190 g of Sipernat™-340 silica were mixed in a container and then charged into an autoclave after mixing. The mixture had the following molar composition (each component measured ±5% or less):

| | |
|---|---|
| $SiO_2/Al_2O_3$ | 470 |
| $H_2O/SiO_2$ | 10.7 |
| $OH/SiO_2$ | 0.16 |
| $Na/SiO_2$ | 0.16 |
| n-PA/Si | 0.25 |

The mixture was mixed and reacted at 99° C. at 350 rpm for 48 hours. The resulting reaction slurry was discharged and stored in a container. The XRD pattern of the as-to synthesized material showed the typical pure phase of ZSM-5 topology. The SEMs of the as-synthesized material show that the material was composed of mixture of crystals with uniform crystal size of about 0.3 micron. The as-synthesized crystals had a $SiO_2/Al_2O_3$ molar ratio of about 450 and Na of about 0.18 wt %.

A portion of the zeolite in the sodium form was used to prepare a 65 wt % zeolite/35 wt % silica particle. 65 parts by weight of zeolite were mulled with 35 parts by weight of silica. The silica was equally supplied by Ultrasil™ silica and by Ludox™ HS-40. Sufficient water was added to produce a mull mix of about 62 wt % solids. The material was extruded into 1/16 inch cylinders. After drying, the sample was subjected to a first calcining step by heating to 482° C. in nitrogen and holding for three hours. The atmosphere was then gradually changed to 1.1, 2.1, 4.2, and 8.4% oxygen in four stepwise increments. Each step was followed by a thirty minute hold. The temperature was increased to 537° C., the oxygen content was increased to 16.8%, and the material was held at 537° C. for 6 hours and cooled. This completed the first calcining step of the catalyst synthesis.

A 40 gram portion was impregnated with silver nitrate and dried for 4 hours at 121° C. It was then impregnated with tetraamine platinum nitrate and dried for 4 hours at 121° C. The impregnated extrudate was dried at 121° C. then subjected to a second calcining step in which the catalyst was calcined for 3 hours in air at 350° C. The catalyst contained about 0.21 wt % Ag and about 0.33 wt % Pt by XRF. The zeolite has an Alpha Value from 5 to 10, and a Constraint Index from 3 to 5, both calculated without the Ag and/or Pt.

Example 1.1: A portion of the material of Example 1.0 was subjected to additional calcination as part of the second calcining step by further calcining the portion in air in a ceramic dish in an electric muffle furnace. The sample was placed in the oven at ambient temperature and heated at 5° C./minute to a temperature of 425° C. and held at that temperature for 4.0 hours, after which the oven was then turned off and allowed to cool to room temperature, or about 23° C.

Example 1.2: A portion of the material of Example 1.0 was subjected to additional calcination as part of the second calcining step by further calcining the portion in air in a ceramic dish in an electric muffle furnace. The sample was placed in the oven at ambient temperature and heated at 5° C./minute to a temperature of 500° C. and held at that temperature for 4.0 hours, after which the oven was then turned off and allowed to cool to 23° C.

Example 1.3: A portion of the material of Example 1.0 was subjected to additional calcination as part of the second calcining step by further calcining the portion in air in a ceramic dish in an electric muffle furnace. The sample was placed in the oven at ambient temperature and heated at 5° C./minute to a temperature of 575° C. and held at that temperature to for 4.0 hours, after which the oven was then turned off and allowed to cool to 23° C.

Example 1.4: A portion of the material of Example 1.0 was subjected to additional calcination as part of the second calcining step by further calcining the portion in air in a ceramic dish in an electric muffle furnace. The sample was placed in the oven at ambient temperature and heated at 5° C./minute to a temperature of 650° C. and held at that temperature for 4.0 hours, after which the oven was then turned off and allowed to cool to 23° C.

Example 1.5: A portion of the material of Example 1.0 was subjected to additional calcination as part of the second calcining step by further calcining the portion in air in a ceramic dish in an electric muffle furnace. The sample was placed in the oven at ambient temperature and heated at 5° C./minute to a temperature of 725° C. and held at that temperature for 4.0 hours, after which the oven was then turned off and allowed to cool to 23° C.

Example 2.0: Comparative example calcined 3 hours in air at 350° C., Cu/Pt. A mixture with about 22% solids was prepared from 8,800 g of DI water, 600 g of 50% NaOH solution, 26 g of 43% Sodium Aluminate solution, 730 g of n-propyl amine 100% solution, 20 g of ZSM-5 seed crystals, and 3,190 g of Sipernat™-340 silica were mixed in a container and then charged into an autoclave after mixing. The mixture had the following molar composition (each component measured ±5% or less):

| | |
|---|---|
| $SiO_2/Al_2O_3$ | 470 |
| $H_2O/SiO_2$ | 10.7 |
| $OH/SiO_2$ | 0.16 |
| $Na/SiO_2$ | 0.16 |
| n-PA/Si | 0.25 |

The mixture was mixed and reacted at 99° C. at 350 rpm for 72 hours. The resulting reaction slurry was discharged and stored in a 5-gal pail container. The XRD pattern of the as-synthesized material showed the typical pure phase of ZSM-5 topology. The material was composed of mixture of crystals with size of 0.5-1 micron. The as-synthesized crystals had a $SiO_2/Al_2O_3$ molar ratio of about 467 and Na of about 0.25 wt %.

A portion of the zeolite in the sodium form was used to prepare a 65 wt % zeolite/35 wt % silica particle. 65 parts by weight of zeolite were mulled with 35 parts by weight of silica. The silica was equally supplied by Aerosil™ 200 and by Ludox™ LS. Sufficient water was added to produce a mull mix of about 66 wt % solids. The material was extruded into 1/16 inch cylinders. After drying, the sample was subjected to a first calcining step by heating to 482° C. in nitrogen and holding for three hours. The atmosphere was then gradually changed to 1.1, 2.1, 4.2, and 8.4% oxygen in four stepwise increments. Each step was followed by a thirty minute hold. The temperature was increased to 538° C., the oxygen content was increased to 16.8%, and the material was held at 538° C. for 6 hours and cooled. This completed the first calcining step of the catalyst synthesis.

A 130 gram portion was impregnated with copper nitrate and dried for 4 hours at 121° C. It was then impregnated with tetraamine platinum nitrate and dried for 4 hours at 121° C. The impregnated extrudate was dried at 121° C. then subjected to a second calcining step in which the catalyst was calcined for 3 hours in air at 350° C. The catalyst contained about 0.27 wt % Cu and about 0.30 wt % Pt by XRF. The zeolite has an Alpha Value from 5 to 10, and a Constraint Index from 3 to 5, both calculated without the Cu and/or Pt.

Example 2.1: A portion of the material of Example 2.0 was subjected to additional calcination as part of the second calcining step by further calcining in air in a ceramic dish in an electric muffle. The sample was placed in the oven at ambient temperature and heated at 5° C./minute to a temperature of 600° C. and held at that temperature for 4.0 hours, after which the oven was then turned off and allowed to cool to 23° C.

Example 2.2: A portion of the material of Example 2.0 was subjected to additional calcination as part of the second calcining step by further calcining in air in a ceramic dish in an electric muffle. The sample was placed in the oven at ambient temperature and heated at 5° C./minute to a temperature of 650° C. and held at that temperature for 4.0 hours, after which the oven was then turned off and allowed to cool to 23° C.

Example 2.3: A portion of the material of Example 2.0 was subjected to additional calcination as part of the second calcining step by further calcining in air in a ceramic dish in an electric muffle furnace. The sample was placed in the oven at ambient temperature and heated at 5° C./minute to a temperature of 700° C. and held at that temperature for 4.0 hours, after which the oven was then turned off and allowed to cool to 23° C.

Example 2.4: A portion of the material of Example 2.0 was subjected to additional calcination as part of the second calcining step by further calcining in air in a ceramic dish in an electric muffle furnace. The sample was placed in the oven at ambient temperature and heated at 5° C./minute to a temperature of 750° C. and held at that temperature for 4.0 hours, after which the oven was then turned off and allowed to cool to 23° C.

Example 3.0: Comparative example calcined 3 hours in air at 538° C., Ag/Pt. The zeolite of Comparative 1 in the sodium form was used to prepare a 65 wt % zeolite/35 wt % silica particle. 65 parts by weight of zeolite were mulled with 35 parts by weight of silica. The silica was equally supplied by Ultrasil™ silica and by Ludox™ HS-40. Sufficient water was added to produce a mull mix of about 63 wt % solids. The material was extruded into 1/16 inch cylinders. After drying, the sample was subjected to a first calcining step by heated to 482° C. in nitrogen and held for three hours. The atmosphere was then gradually changed to 1.1, 2.1, 4.2, and 8.4% oxygen in four stepwise increments. Each step was followed by a thirty minute hold. The temperature was increased to 538° C., the oxygen content was increased to 16.8%, and the material was held at 538° C. for 6 hours and cooled. This completed the first calcining step of the catalyst synthesis.

A 110 gram portion was impregnated with silver nitrate and dried for 4 hours at 121° C. It was then impregnated with tetraamine platinum nitrate and dried for 4 hours at 121° C. The impregnated extrudate was dried at 121° C. then subjected to a second calcining step in which the catalyst was calcined for 3 hours in air at 538° C. The catalyst contained about 0.13 wt % Ag and about 0.31 wt % Pt by XRF. The zeolite has an Alpha Value from 5 to 10, and a Constraint Index from 3 to 5, both calculated without the Ag and/or Pt.

Example 3.1: A portion of the material of Example 3.0 was subjected to additional calcination as part of the second calcining step by further calcining in air in a ceramic dish in an electric muffle. The sample was placed in the oven at ambient temperature and heated at 5° C./minute to a temperature of 600° C. and held at that temperature for 5.0 hours, after which the oven was then turned off and allowed to cool to 23° C.

A portion of each of the catalysts prepared in Examples 1.0 to 3.1 were evaluated for performance in the conversion of n-pentane to cyclic C5s including cyclopentadiene. The catalyst (0.25 g crushed and sieved to 20 to 40 mesh) was physically mixed with high-purity SiC (40-60 mesh) and loaded into a 9 mm ID, 13 mm OD, 483 mm long quartz reactor. The amount of SiC was adjusted so that the overall length of the catalyst bed was 152 mm. The catalyst bed was held in place with quartz wool and the reactor void space was loaded with coarse SiC particles. The reactor was loaded onto the unit and pressure tested to ensure no leaks.

The catalyst was dried for 1 hour under helium (145 mL/min, 30 psig, 250° C.) then reduced for 4 hours under $H_2$ (270 mL/min, 30 psig, 500° C.). The catalyst was then tested for performance with feed of n-pentane, $H_2$, and balance helium, 3.3 psia $C_5H_{12}$, 1.0 molar $H_2$:$C_5H_{12}$, and 30 psig total. The catalyst was tested at 575° C. at an n-pentane WHSV=30 $h^{-1}$.

The 8 hour average yield of products (C %) is shown in the Table 1 below; cC5 total is the sum of cyclopentadiene, cyclopentene and cyclopentane.

TABLE 1

| Example | Additional Second Step Calcination | | Yields (C %; 8 hr average values) | | | | |
| --- | --- | --- | --- | --- | --- | --- | --- |
| | Time (hrs) | Temp (° C.) | C1 total | C2-C4 total | iC5 total | cC5 total | cyclo-pentadiene |
| 1.0 | none | none | 0.31 | 2.29 | 0.76 | 22.26 | 17.49 |
| 1.1 | 4.0 | 425 | 0.43 | 3.07 | 1.03 | 26.07 | 19.77 |
| 1.2 | 4.0 | 500 | 0.59 | 4.17 | 1.39 | 28.83 | 21.87 |
| 1.3 | 4.0 | 575 | 0.63 | 4.43 | 1.57 | 29.61 | 21.49 |
| 1.4 | 4.0 | 650 | 0.59 | 4.30 | 1.53 | 29.23 | 21.69 |
| 1.5 | 4.0 | 725 | — | — | — | — | — |
| 2.0 | none | none | 0.75 | 5.08 | 2.44 | 16.68 | 11.35 |
| 2.1 | 4.0 | 600 | 0.80 | 7.20 | 3.85 | 26.66 | 15.48 |
| 2.2 | 4.0 | 650 | 0.84 | 5.46 | 3.55 | 26.36 | 16.00 |
| 2.3 | 4.0 | 700 | 0.72 | 4.82 | 3.27 | 17.53 | 11.31 |
| 2.4 | 4.0 | 750 | 0.33 | 3.80 | 2.52 | 3.72 | 2.55 |
| 3.0 | none | none | 0.47 | 3.44 | 1.17 | 29.73 | 24.58 |
| 3.1 | 5.0 | 600 | 0.59 | 4.05 | 1.32 | 36.80 | 30.28 |

Examples 3.2-3.9: A portion of the material of Example 3.0 was subjected to additional calcination as part of the second calcining step by further calcining in a reactor prior to catalytic performance testing. The catalyst (0.25 g for each sample crushed and sieved to 20 to 40 mesh) was physically mixed with high-purity SiC (40 to 60 mesh) and loaded into a 9 mm ID, 13 mm OD, 483 mm long quartz reactor. The amount of SiC was adjusted so that the overall length of the catalyst bed was 152 mm. The catalyst bed was held in place with quartz wool and the reactor void space was loaded with coarse SiC particles. The reactor was loaded onto the unit and pressure tested to ensure no leaks. The catalyst was heated from ambient temperature to Temp$^C$ (at four temperatures as shown in the table) at 10° C./minute in helium flowing at 246 standard mL/minute, at 30 psig. The catalyst was then held at temperature for Time$^C$ (at two time durations as shown in the table) in 10 mol % oxygen, 90 mol % helium flowing at 312 standard mL/minute, at 30 psig.

The catalyst was then allowed to cool under helium (145 mL/min, 30 psig) to 500° C. then reduced for 4 hours under $H_2$ (270 mL/min, 30 psig, 500° C.). The catalyst was then tested for performance with feed of n-pentane, $H_2$, and balance helium, 3.3 psia $C_5H_{12}$, 1.0 molar $H_2$:$C_5H_{12}$, and 30 psig total. The catalyst was tested at 575° C. at an n-pentane WHSV=30 $h^{-1}$.

The 8 hour average yield of products (C %) is shown in the Table 2 below; cC5 total is the sum of cyclopentadiene, cyclopentene and cyclopentane.

TABLE 2

| Example | Additional Second Step Calcination | | Yields (C %; 8 hr average values) | | | | |
|---|---|---|---|---|---|---|---|
| | Time$^C$ (hrs) | Temp$^C$ (° C.) | C1 total | C2-C4 total | iC5 total | cC5 total | cyclo-pentadiene |
| 3.2 | 0.5 | 600 | 0.53 | 3.99 | 1.55 | 31.79 | 25.91 |
| 3.3 | 0.5 | 650 | 0.61 | 4.51 | 1.70 | 35.04 | 28.92 |
| 3.4 | 0.5 | 700 | 0.62 | 4.52 | 1.60 | 35.34 | 29.13 |
| 3.5 | 0.5 | 725 | 0.59 | 4.34 | 1.48 | 33.66 | 27.58 |
| 3.6 | 1.0 | 600 | 0.58 | 4.06 | 1.53 | 34.17 | 27.60 |
| 3.7 | 1.0 | 650 | 0.73 | 5.15 | 1.78 | 36.91 | 28.83 |
| 3.8 | 1.0 | 700 | 0.71 | 5.01 | 1.72 | 38.27 | 30.20 |
| 3.9 | 1.0 | 725 | 0.72 | 4.98 | 1.56 | 37.36 | 30.68 |

Part 2 Examples: Impact of First Step Calcining

The microporous zeolites described herein, such as ZSM-5 crystals used in catalysts such as described herein, are synthesized using an organic structure directing agent (OSDA) such as an organic amine, (e.g., n-propylamine) It has now been discovered that the methodology for removing the OSDA from the microporous crystalline metallosilicate catalyst in the first calcining step impacts the performance of the finished catalyst used in a process for the cyclization of acyclic C5s. While not wishing to be bound by theory, it is believed that removal of the OSDA in a manner to maximize the concentration of silanol sites within the zeolite crystal is advantageous for achieving high Pt dispersion on the silanol sites. There may be other means to remove the OSDA while preserving silanols such as by liquid phase extraction or use of a strong oxidizing agent such as ozone or NOx. The following examples demonstrate how the means of such removal, similar to the first step calcination processes described herein, can be effected.

Example 1: Synthesis of ZSM-5

A 22% solids mixture containing DI water, 50% NaOH solution, 43% Sodium Aluminate solution, n-propyl amine 100% solution, ZSM-5 seed crystals, and Ultrasil™ silica was charged into an autoclave after mixing. The mixture had the following molar composition (each component measured ±5% or less):

| | |
|---|---|
| $SiO_2/Al_2O_3$ | 470 |
| $H_2O/SiO_2$ | 10.73 |
| $OH/SiO_2$ | 0.16 |
| $Na/SiO_2$ | 0.16 |
| n-PA/Si | 0.25 |

The mixture was mixed and reacted at 210° F. (99° C.) at 185 rpm for 72 hours. The resulting reaction slurry was discharged and stored in a 30-gal pail container. The resulting slurry was flocced, decanted, and then filtered/washed overnight before drying. The product zeolite consisted of distinct crystals with size of 1 micron. The resulting ZSM-5 crystals had a Na content of about 0.48 wt % after correcting for % solids, Na/Al (molar ratio) of about 3, and a carbon content of 5.29 wt %.

Example 2: Synthesis of ZSM-5

A 20% solids mixture containing DI water, 50% NaOH solution, 43% Sodium Aluminate solution, n-propyl amine 100% solution, ZSM-5 seed crystals, and Ultrasil™ silica was charged to an autoclave. The reaction mixture had the following molar composition (each component measured ±5% or less):

| | |
|---|---|
| $SiO_2/Al_2O_3$ | 470 |
| $H_2O/SiO_2$ | 12.3 |
| $OH/SiO_2$ | 0.16 |
| $Na/SiO_2$ | 0.16 |
| n-PA/Si | 0.25 |

The mixture was mixed and reacted at 220° F. (110° C.) at 75 rpm for about 40 hours. Residual n-PA in the mother liquor was removed by flashing at 240° F. after completion of crystallization. The resulting slurry was then transfer to a decanter for floccing and decantation. The flocced slurry was then filtered, washed and dried. The XRD pattern of the as-synthesized material showed the typical pure phase of ZSM-5 topology. SEM of the as-synthesized material showed that the material was composed of mixture of distinct crystals with size of 0.5 micron. The resulting ZSM-5 crystals had a Na content of about 0.49 wt % after correcting for % solids, Na/Al (molar ratio) of about 2.54, and a carbon content of 1.84 wt %.

Example 3: Hybrid Calcination of ZSM-5

A sample of the ZSM-5 crystal prepared in Example 1 was subjected to a first calcination step by calcining for 9 hours in nitrogen at 900° F. The atmosphere was then gradually changed to 1.1, 2.1, 4.2, and 8.4% oxygen in four stepwise increments. Each step was followed by a thirty minute hold. The temperature was increased to 1000° F., the oxygen content was increased to 16.8%, and the material was held at 1000° F. for 6 hours. Carbon content on the calcined zeolite was <0.05%.

Example 4: Nitrogen Calcination of ZSM-5

A sample of the ZSM-5 crystal prepared in Example 1 was subjected to a first calcination step by ramping the catalyst temperature at 300° F./min in flowing nitrogen from room temperature to 482° C. (900° F.) and then holding for 1 hour. Carbon content on the calcined zeolite was <0.05%.

Example 5: Nitrogen Calcination of ZSM-5

A sample of the ZSM-5 crystal prepared in Example 1 was subjected to a first calcination step by ramping the catalyst temperature at 300° F./min in flowing nitrogen from room temperature to 482° C. (900° F.) and then holding for 6 hour. Carbon content on the calcined zeolite was 0.059%.

Example 6: Air Calcination of ZSM-5

A sample of the ZSM-5 crystal prepared in Example 1 was subjected to a first calcination step by inserting the catalyst into a tube furnace that was pre-heated to 450° C. (842° F.) and then holding in continuous air flow at this temperature for 0.75 hour. Carbon content on the calcined zeolite was <0.05%.

Example 7: Air Calcination of ZSM-5

A sample of the ZSM-5 crystal prepared in Example 1 was subjected to a first calcination step by inserting the catalyst into a tube furnace that was pre-heated to 550° C. (1022° F.)

and then holding in continuous air flow at this temperature for 0.75 hour. Carbon content on the calcined zeolite was 0.06%.

Example 8: Air Calcination of ZSM-5

A sample of the ZSM-5 crystal prepared in Example 1 was subjected to a first calcination step by inserting the catalyst into a tube furnace that was pre-heated to 600° C. (1112° F.) and then holding in continuous air flow at this temperature for 0.75 hour. Carbon content on the calcined zeolite was <0.05%.

Example 9: Air Calcination of ZSM-5

A sample of the ZSM-5 crystal prepared in Example 1 was subjected to a first calcination step by inserting the catalyst into a tube furnace that was pre-heated to 650° C. (1202° F.) and then holding in continuous air flow at this temperature for 0.75 hour. Carbon content on the calcined zeolite was <0.05%.

Example 10: Air Calcination of ZSM-5

A sample of the ZSM-5 crystal prepared in Example 1 was subjected to a first calcination step by inserting the catalyst into a tube furnace that was pre-heated to 700° C. (1292° F.) and then holding in continuous air flow at this temperature for 0.75 hour. Carbon content on the calcined zeolite was <0.05%.

Example 11: Impregnation of 0.5% Pt on Calcined ZSM-5

Samples of calcined crystals prepared in Examples 3, 4, 5, 7, and 10 were impregnated with Pt using Platinum Tetraamine nitrate to a target of 0.5% Pt based on the weight of ZSM-5 crystal. After impregnation, samples were dried at 250° F. and then subjected to a second calcination step by calcining at 660° F. for 3 hours. XRF analysis showed the following Na and Pt concentrations in Table 3:

TABLE 3

| Sample | Starting Material | Na (wt %) | Pt (wt %) |
|---|---|---|---|
| 11A | 3 | 0.387 | 0.479 |
| 11B | 4 | 0.372 | 0.522 |
| 11C | 5 | 0.424 | 0.537 |
| 11D | 7 | 0.311 | 0.507 |
| 11E | 10 | 0.365 | 0.497 |

Example 12: Conversion of n-pentane

A sample of the catalysts prepared in Example 11 were evaluated for performance in the conversion of n-pentane to CPD. The catalyst (0.25 g crushed and sieved to 20-40 mesh) was physically mixed with high-purity SiC (40-60 mesh) and loaded into a 9 mm ID, 13 mm OD, 19" long quartz reactor. The amount of SiC was adjusted so that the overall length of the catalyst bed was 6 in. The catalyst bed was held in place with quartz wool and the reactor void space was loaded with coarse SiC particles. The reactor was loaded onto the unit and pressure tested to ensure no leaks.

The catalyst was dried for 1 hour under helium (145 mL/min, 30 psig, 250° C.) then reduced for 4 hours under $H_2$ (270 mL/min, 30 psig, 500° C.). The catalyst was then tested for performance with feed of n-pentane, $H_2$, and balance helium, 3.3 psia C5H12, 1.0 molar $H_2:C_5H_{12}$, and 30 psig total. The catalyst was tested at 575° C. at an n-pentane WHSV=15 $h^{-1}$.

After 30 hours of reaction, the catalyst was exposed to $H_2$ for 30 minutes (275 mL/min, 30 psig, 575° C.) and then to helium for 20 minutes (260 mL/min, 30 psig, 475° C.). The catalyst was then rejuvenated in $O_2$/He mixture (195 ml/min, 45 psig, 475° C.) with increasing $O_2$ concentration of 0.5-4% for a total of 5 hours (0.5% $O_2$ for 1 hour, 0.75% $O_2$ for 20 minutes, 1.0% $O_2$ for 20 minutes, 1.5% $O_2$ for 20 minutes, 2.0% $O_2$ for 20 minutes, 3.0% $O_2$ for 20 minutes, and 4% $O_2$ for 2 hours and 20 minutes). After rejuvenation, the catalyst was exposed to helium for 30 minutes (270 mL/min, 30 psig, 500° C.) and then reduced at conditions previously mentioned before beginning the next cycle of reaction.

The 15 hour average yield of cyclic C5 products (CPD, cyclopentene and cyclopentane) (C %) measured during cycle 3 is shown in the Table 4 below.

TABLE 4

| Sample | Cyclic C5 Yield (%) |
|---|---|
| 11A | 36 |
| 11B | 37 |
| 11C | 34 |
| 11D | 40 |
| 11E | 45 |

The samples prepared by air calcination at high temperatures and short times have to higher cyclic C5 yields than materials prepared using longer lower temperature calcinations.

Example 13: Characterization of ZSM-5 Silanol Content

A sample of ZSM-5 crystal prepared in Examples 7 through 10 were analyzed for silanol content using the following FTIR Spectroscopy method.

For the Infrared (IR) measurement of adsorbed pyridine, the samples were ground in an agate mortar and pressed into thin self-supporting wafers. The pressure ranged between 1.5 and 2 metric tons corresponding to a pressure of about 240 to 320 bar applied to the dies. Specific wafer weights ranged from 25 to 40 mg/cm². The samples were placed into an IR-transmission cell equipped with $CaF_2$ windows. Samples were pretreated in-situ by evacuation for 2 h at 400° C. at a pressure of about $10^{-6}$ Torr. The samples were subsequently exposed for 30 min to about 10 Torr vapor pressure of pyridine at 150° C. followed by evacuation for 30 min at 150° C. at a pressure of about $10^{-5}$ Torr. For the collection of IR spectra the IR cuvette was transferred into a Bruker Vertex™ 70 FTIR spectrometer. Spectra were taken at room temperature at 2 $cm^{-1}$ resolution accumulating 512 scans.

For the characterization of the silanol content, the pyridine band at about 1445 $cm^{-1}$ was integrated and divided by the integrated area of silica overtone and combination bands measured after evacuation at 400° C. The integrated silica band intensity was evaluated between spectral minima occurring at around 2100 $cm^{-1}$ (to the high frequency side of the silica bands) and around 1740 $cm^{-1}$ (to the low frequency side of the silica bands).

Example 14: Characterization of Silanol Content

ZSM-5 crystals described in examples 7, 8, 9, and 10 were analyzed for their silanol content using the IR test described in example 13. Without being bound by any particular theory the pyridine band at 1445 $cm^{-1}$ can be ascribed to silanol bonded pyridine and was chosen for the evaluation of the silanol content. Table 3 reports the integrated area of the band at 1445 $cm^{-1}$ divided by the integrated silica band area after 400° C. evacuation.

TABLE 5

| Example | Calcination temperature of ZSM-5 crystal, [° C.] | Integrated band area at 1445 $cm^{-1}$ divided by integrated silica band area |
| --- | --- | --- |
| 7 | 550 | 0.035 |
| 8 | 600 | 0.059 |
| 9 | 650 | 0.085 |
| 10 | 700 | 0.026 |

It can be seen that the silica normalized band area at 1445 $cm^{-1}$ was higher at intermediate calcination temperatures of 600° C. and 650° C. compared to samples that were calcined at lower (550° C.) or higher (700° C.) temperatures. This was surprising as one might expect a continuous decline in silanol group content due to condensation of silanol groups with rising calcination temperature.

Fluidizable Particles

It is contemplated that the zeolites crystals such as but not limited to those discussed above could be formed into fluidizable particles. OSDA removal may be performed before or after forming into particles but preferably performed prior to metallization. Such materials could be formed by deagglomerating the sodium zeolite crystals The sodium zeolite crystals could then be mixed with matrix material which could be a mixture of inorganic materials such as silica, alumina, titania or zirconia and clays such as kaolin and bentonite to form an aqueous slurry. The matrix could be peptized. Any surface acidity of alumina in the binder is either minimized or controlled through the addition of alkaline metals, alkaline earth metals or a source of phosphorus to the spray dry slurry. The slurry could be dried such as by spray drying and then calcined to form a fluid powder of, for example, less than 200 microns in diameter. Optionally, the acidity of the alumina could be controlled by post-treatment with sources of alkaline metals or alkaline earth metals such as by impregnation. The fluidizable particles can then be treated with sources of desired metals such as platinum, platinum and silver or platinum and copper to form metal containing, formulated sodium ZSM-5

As used herein, "consisting essentially of" for the catalyst means that the catalyst may include minor amounts of ingredients not named, but does not include any other ingredients, or made from any other essential calcining steps, not named that would influence its catalytic activity towards conversion of acyclic alkanes to cyclic alkanes to an analytically significant extent such as ±1, 2, or 5 wt % of a final product or overall rate.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have to been illustrated and described, various modifications can be made without departing from the spirit and scope of the invention.

The invention claimed is:

1. A catalyst comprising: (i) a microporous crystalline metallosilicate having a Constraint Index of 12 or less, (ii) a binder, (iii) a Group 1 alkali metal or a compound thereof and/or a Group 2 alkaline earth metal or a compound thereof, (iv) a Group 10 metal or a compound thereof, and, (v) optionally a Group 11 metal or a compound thereof; wherein the catalyst is calcined in a first calcining step of calcining the catalyst before the addition of the Group 10 metal or compound thereof and optionally the Group 11 metal or compound thereof; and wherein the first calcining step includes heating the catalyst to temperatures of greater than 500° C.; and calcinating the catalyst in a second calcining step after the addition of the Group 10 metal or compound thereof and optionally the Group 11 metal or compound thereof wherein the second calcining step includes heating the catalyst to temperatures of greater than 400° C.

2. The catalyst of claim 1, wherein the catalyst is calcined in either first or second calcining steps in a rotary calciner or a fixed bed calciner in an air atmosphere.

3. The catalyst of claim 1, wherein the first temperature is greater than 525° C.; and wherein the second temperature is greater than 450° C.

4. The catalyst of claim 1, wherein the catalyst is calcined in either the first or second calcining steps by heating at 500° C. to 800° C. and then holding in continuous air (oxygen/nitrogen) flow at this temperature for 0.5 to 1 hour.

5. The catalyst of claim 1, wherein the second calcination step is performed at least partially in conjunction with the process unit where the converting of acyclic C5s to cyclic C5 compounds is performed.

6. The catalyst of claim 1, wherein the calcined catalyst presents an IR band intensity ratio greater than about 0.06 of the integrated IR band area at 1445 $cm^{-1}$ measured after adsorption and evacuation of pyridine at 150° C. divided by the integrated IR band area of silica bands between 2100 $cm^{-1}$ and 1740 $cm^{-1}$ measured after evacuation at 400° C.

7. The catalyst of claim 1, wherein the catalyst is formed into one or more of the shapes of extrudates (cylindrical, lobed, asymmetric lobed, spiral lobed), spray dried particles, oil drop particles, mulled particles, spherical particles, and/or wash coated substrates; wherein the substrates may be extrudates, spherical particles, foams, microliths and/or monoliths.

8. The catalyst of claim 1, wherein the microporous crystalline metallosilicate comprises a metallosilicate framework type selected from the group consisting of MWW, MFI, LTL, MOR, BEA, TON, MTW, MTT, FER, MRE, MFS, MEL, DDR, EUO, and FAU.

9. The catalyst of claim 1, wherein the microporous crystalline metallosilicate is an aluminosilicate selected from the group consisting of Zeolite beta, mordenite, faujasite, Zeolite L, ZSM-5, ZSM-11, ZSM-30, ZSM-22, ZSM-23, ZSM-35, ZSM-48, ZSM-50, ZSM-57, ZSM-58, MCM-22 family material, and mixtures thereof.

10. The catalyst of claim 1, wherein the binder is selected from silica, titania, zirconia, alkali metal silicates, Group 13 metal silicates, carbides, nitrides, aluminum phosphate, aluminum molybdate, aluminate, surface passivated alumina, or mixtures thereof.

11. The catalyst of claim 1, wherein the molar ratio of the Group 1 alkali metal to aluminum is at least 1, and/or the molar ratio of the Group 2 alkaline earth metal to aluminum is at least 1 and the Group 1 alkali metal is selected from the group consisting of lithium, sodium, potassium, rubidium, cesium, and mixtures of two or more thereof, and/or the Group 2 alkaline earth metal is selected from the group consisting of beryllium, magnesium, calcium, strontium, barium, and mixtures thereof.

12. The catalyst of claim 1, wherein the catalyst has an Alpha Value of less than 14.

13. The catalyst of claim 1, wherein the Group 10 metal is platinum, and wherein the platinum is derived from compounds selected from the group consisting of platinum nitrate, chloroplatinic acid, platinous chloride, platinum amine compounds, tetraamine platinum hydroxide, and mixtures thereof.

14. The catalyst of claim 1, wherein the optional Group 11 metal is included, and the Group 11 metal includes copper and/or silver, wherein the copper is derived from copper nitrate, copper nitrite, copper acetate, copper hydroxide, copper acetylacetonate, copper carbonate, copper lactate, copper sulfate, copper phosphate, copper chloride, or mixtures thereof, and wherein the silver is derived from silver nitrate, silver nitrite, silver acetate, silver hydroxide, silver acetylacetonate, silver carbonate, silver lactate, silver sulfate, silver phosphate, or mixtures thereof.

15. The catalyst of claim 1, wherein the catalyst is combined with acyclic $C_5$ s to form cyclic $C_5$ compounds including cyclopentadiene.

16. An article formed from cyclic $C_5$ compounds of claim 15, wherein the article is derived from a Diels-Alder reaction of the cyclic $C_5$ compounds with a double bond containing compound.

17. The article of claim 16, wherein the cyclic $C_5$ compounds are selected from the group consisting of cyclopentadiene, dicyclopentadiene, cyclopentene, cyclopentane, substituted norbornenes, Diels Alder (conjugated diene+ substituted diene) reaction derivatives of cyclopentadiene, cyclic olefin copolymers, cyclic olefin polymers, polycyclopentene, unsaturated polyester resins, hydrocarbon resin tackifiers, formulated epoxy resins, polydicyclopentadiene, metathesis polymers of norbornene or substituted norbornenes or dicyclopentadiene, and combinations thereof.

18. A process to make a catalyst comprising: (i) providing a microporous crystalline metallosilicate having a Constraint Index of 12, or 10, or 8, or 6 or less, (ii) a binder, (iii) a Group 1 alkali metal or a compound thereof and/or a Group 2 alkaline earth metal or a compound thereof, (iv) a Group 10 metal or a compound thereof, and, (v) optionally a Group 11 metal or a compound thereof; calcining in a first calcination step the combination of materials before the addition of the Group 10 metal or compound and optional Group 11 metal or compound thereof; adding the Group 10 metal or compound thereof and then calcining in a second calcination step prior to addition of the optional Group 11 metal; adding the optional Group 11 metal or compound thereof and then calcining in a third calcination step wherein calcining includes heating the catalyst to temperatures of greater than 500° C. in the first calcination step and includes heating the catalyst to temperatures of greater than 400° C. in the second calcination step and includes heating the catalyst to temperatures of greater than 500° C. in the third calcination step.

19. The process of claim 18, wherein the first calcination step takes place at a temperature greater than 525° C.; wherein the second calcination step takes place at a temperature greater than 425° C.; and wherein the third calcination step takes place at a temperature greater than 550° C.

20. The process of claim 18, wherein the catalyst is calcined in any of the calcination steps by heating at 500° C. to 800° C. and then holding in continuous air (oxygen/nitrogen) flow at this temperature for 0.5 to 1 hour.

* * * * *